US012766149B2

(12) United States Patent
Vasilikos et al.

(10) Patent No.: US 12,766,149 B2
(45) Date of Patent: Oct. 20, 2026

(54) RIBOFLAVIN FOR TREATING COLLAGENOUS TISSUES IN THE DISEASES OF JOINTS, PARTICULARLY OF INTERVERTEBRAL DISCS

(71) Applicant: Albert-Ludwigs-Universitat Freiburg, Freiburg (DE)

(72) Inventors: Ioannis Vasilikos, Freiburg (DE); Ulrich Hubbe, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 1088 days.

(21) Appl. No.: 17/294,143

(22) PCT Filed: Nov. 18, 2019

(86) PCT No.: PCT/EP2019/081595
§ 371 (c)(1),
(2) Date: May 14, 2021

(87) PCT Pub. No.: WO2020/099673
PCT Pub. Date: May 22, 2020

(65) Prior Publication Data

US 2022/0016125 A1 Jan. 20, 2022

(30) Foreign Application Priority Data

Nov. 16, 2018 (DE) ......................... 102018128822.0

(51) Int. Cl.
*A61K 31/525* (2006.01)
*A61N 5/06* (2006.01)

(52) U.S. Cl.
CPC .......... *A61K 31/525* (2013.01); *A61N 5/0601* (2013.01); *A61N 2005/0661* (2013.01)

(58) Field of Classification Search
CPC .................................................... A61K 31/525
See application file for complete search history.

(56) References Cited

U.S. PATENT DOCUMENTS

| | | | |
|---|---|---|---|
| 6,723,335 B1 | 4/2004 | Moehlenbruck et al. | |
| 2013/0338650 A1* | 12/2013 | Jester .................. | A61F 9/00825 606/5 |
| 2016/0303284 A1 | 10/2016 | Borde et al. | |
| 2017/0274218 A1* | 9/2017 | Schmocker ............ | A61N 5/062 |

FOREIGN PATENT DOCUMENTS

WO 2004073563 A2 9/2004

OTHER PUBLICATIONS

Meek et.al.; PLoS One, Aug. 2011, vol. 6, Issue 8, e22405 (Year: 2011).*
Meek et.al.; PLoS One, Aug. 2011, vol. 6, Issue 8, p. 22405 (Year: 2011).*
Meek et.al.; PLoS One, Aug. 2011, vol. 6, Issue 8, 22405 (Year: 2011) (Year: 2011).*
Anisel et.al. Pharmaceutical Dosage Forms and Drug Delivery Systems 7th edition, 1999 (Year: 1999).*
Int'l. Search Report for PCT/EP2019/081595, dated Apr. 15, 2019.

* cited by examiner

*Primary Examiner* — Noble E Jarrell
*Assistant Examiner* — Rehana Ismail
(74) *Attorney, Agent, or Firm* — MaxGoLaw PLLC

(57) ABSTRACT

Riboflavin for use as a medicament in the treatment of a patient with a disease of a diarthrotic, amphiarthrotic or synarthrotic joint, preferably an intervertebral disc disease is provided. The treatment occurs in situ in the patient and includes local administering of riboflavin in a collagenous tissue of the joint and subsequent irradiation with electromagnetic radiation. A method and a kit are also provided for carrying out in-situ crosslinking of a collagenous tissue in the case of a disease of a diarthrotic, amphiarthrotic or synarthrotic joint, preferably an intervertebral disc.

16 Claims, 14 Drawing Sheets

RIBOFLAVIN FOR TREATING COLLAGENOUS TISSUES IN THE DISEASES OF JOINTS, PARTICULARLY OF INTERVERTEBRAL DISCS

The invention relates to riboflavin for use as a medicament in the treatment of a patient with a disease of a diarthrotic, amphiarthrotic or synarthrotic joint, preferably an intervertebral disc disease, wherein the treatment occurs in situ in the patient and comprises local administering of riboflavin in a collagenous tissue of the joint and subsequent irradiation with electromagnetic radiation, preferably UV irradiation or multiphoton irradiation. The invention further relates to a method and a kit for carrying out in-situ crosslinking of a collagenous tissue in the case of a disease of a diarthrotic, amphiarthrotic or synarthrotic joint, preferably an intervertebral disc.

BACKGROUND AND PRIOR ART

The intervertebral disc is a flexible, cartilaginous connection between the vertebrae of the spine. As an elastic joint, the intervertebral discs ensure that the vertebrae can bend, stretch and rotate relative to one another and that the spine can move in a stable manner.

The elasticity and stability of the intervertebral disc is due to the functional interaction of the fiber ring (annulus fibrosus) and the water-rich gelatinous core (nucleus pulposus). In a healthy intervertebral disc, an axial compression leads to a compression of the hydrodynamic nucleus pulposus, which transfers the pressure to the annulus fibrosus surrounding it. The concentric connective tissue fibers of the annulus fibrosus form a high tensile strength sheath, which ensures effective damping.

In the course of a person's life, intervertebral discs are exposed to high pressure loads and a physiological aging process, which can often lead to signs of wear and tear or functional disorders. Vital chondrocytes, which form the gelatinous core and ensure hydraulic permeability, are crucial for a functional and elastic intervertebral disc. Since the intervertebral discs are not supplied by the vascular system, the supply of nutrients requires diffusion and convection, which decreases with age. This severely limits the ability of the cells to repair and divide. Particularly, the hydrodynamic function of the nucleus pulposus decreases with age, which reduces the elasticity of the intervertebral disc.

Capsule ligament injuries, vertebral body fractures or particularly heavy loads can cause additional damage to the annulus fibrosus and lead to a displacement of the nucleus pulposus into the vertebral canal.

In the case of a herniated disc or a disc protrusion, parts of the disc protrude into the spinal canal. While an intervertebral disc bulges in a disc protrusion, a herniated disc is characterized by a complete or partial tear of the annulus fibrosus. When the intervertebral disc emerges into the spinal canal, pressure can be applied to the nerve cords located there. Symptoms of a herniated disc can therefore include severe pain, impaired sensitivity or paralysis.

It is estimated that 80% of the population have back problems and 5-10% develop chronic symptoms (Finch et al. 2006). A major factor in chronic back pain is degeneration of the intervertebral disc. In Germany alone, around 180,000 people each year suffer from a slipped disc.

Various therapeutic approaches are known for the treatment of disc diseases, particularly a herniated disc. In the case of conservative treatment, the aim is to relieve the symptoms by administering painkillers and physiotherapy as well as retraining and, if necessary, to promote a regression of the herniated disc.

Surgical treatment is required if the conservative therapy fails or if progression is particularly severe, and especially if there are signs of paralysis. A part of the prolapsed intervertebral disc is surgically removed to relieve the pressure in the spinal canal. However, this also cannot guarantee that there will be no symptoms. In addition, recurrences can occur and the physiological elasticity of the intervertebral disc is permanently impaired in the affected area.

More recent therapeutic approaches also include regeneration of the gelatinous core by injecting the body's own tissue, injecting an artificial gelatinous core to stabilize the intervertebral disc or replacing the diseased intervertebral disc with an implant.

WO 2004/073563 A2 describes a fusion implant for vertebrae for the treatment of herniated discs. The fusion implant comprises a balloon which is filled with hardenable material to take up the load of the vertebrae. Cement comprising calcium or crosslinkable polymers are disclosed as hardenable materials.

U.S. Pat. No. 6,723,335 B1 discloses therapeutic methods for regenerating intervertebral discs by injecting a fluid matrix or a hydrogel. The fluid matrix is cross-linked from decellularized nucleus pulposus tissue from an external donor or from the same patient with the aid of photo-oxidative catalysts. The crosslinking is carried out in vitro, and then the crosslinked fluid matrix is injected into the intervertebral spaces.

However, the procedures are complex. In addition, a reduced connection between an injected hydrogel or an implant and the endogenous tissue can lead to loss of stability.

WO 2011/002889 A2 and US 2005/0209699 A1 disclose methods for in-situ crosslinking of endogenous collagen tissue in the human body. For this purpose, genipin or proantrocyanidin, among others, are injected into the body's own collagen tissue as crosslinkers in order to stabilize it. At physiological concentrations of the crosslinkers, the crosslinking reaction takes several hours up to a few days, so that there may be intermittent changes in shape or structure of the tissue to be stabilized. Riboflavin is a vitamin from the B complex, but can also be used to crosslink collagen tissues. A photopolymerization catalyzed by riboflavin includes the production of singlet oxygen, which can react with functional groups of the collagen tissue (Min et al. 2002, Huang et al. 2004, Choe et al. 2005). The reaction includes tyrosine residues, which form pi-pi complexes in the collagen and lead to dityrosinecrosslinks (LaBella et al. 1968, Waykole et al. 2009).

Scott McCall et al. have shown that in addition to the singlet oxygen, the carbonyl groups and proteoglycans also play an important role in photopolymerization and support the formation of covalent bonds between collagen-collagen fibers or collagen-proteoglycans (McCall et al. 2010).

In the medical field, the crosslinking property of riboflavin is mainly used to treat keratoconus. Keratoconus is an eye disease that designates the progressive thinning and deformation of the cornea and is one of the most common reasons for a corneal transplant.

In a standard application, a few drops of riboflavin are applied to the callus, such that it can penetrate the underlying tissue layers. The crosslinking reaction is then triggered by means of UV irradiation. In most cases, this can strengthen the cornea so that the course of the disease is stopped (Mahgol Farjadnia et al. 2015, Wollensak et al. 2006, Hafezi et al. 2009).

Recently, the possibility of photoactivation of riboflavin to strengthen the cornea based on multiphoton excitation was reported (Samantha et al. 2017). Instead of using a UV light source, the irradiation takes place by means of a femtolaser at approx. 760 nm, wherein a non-linear two-photon excitation leads to a riboflavin-mediated crosslinking reaction.

A therapeutic potential of riboflavin for the treatment of diseases of diarthrotic, amphiarthrotic or synarthrotic joints, particularly intervertebral disc diseases, has so far only been insufficiently investigated.

OBJECT OF THE INVENTION

In the light of the prior art, it was an object of the invention to provide alternative or improved treatment options in order to treat diseases of diarthrotic, amphiarthrotic or synarthrotic joints, particularly intervertebral disc diseases.

SUMMARY OF THE INVENTION

This object is achieved by the features of the independent claims. The dependent claims relate to preferred embodiments of the invention.

The invention relates preferably to riboflavin for use as a medicament in the treatment of a patient with a disease of a diarthrotic, amphiarthrotic or synarthrotic joint, preferably an intervertebral disc disease, wherein the treatment occurs in situ in the patient and comprises local administering of riboflavin in a collagenous tissue of the joint and subsequent irradiation with electromagnetic radiation.

It is known from the prior art to use riboflavin in the context of treating keratoconus to strengthen collagen tissues. However, it was completely surprising to find that riboflavin is also suitable for in-situ crosslinking of collagenous tissues in the case of a disease of diarthrotic, amphiarthrotic or synarthrotic joints, particularly in the case of intervertebral disc diseases.

The term joints should be understood to mean any anatomical structures that allow a movable connection between bony or cartilaginous skeletal elements.

The joints of the human body can be divided into diarthrotic (discontinuous) and synarthrotic/amphiarthrotic (continuous joints).

Synarthrotic/amphiarthrotic joints are continuous cartilaginous or connective tissue-type bone connections that have no interruption and therefore usually have limited mobility.

The synarthrotic/amphiarthrotic (continuous) joints, which are also referred to as synarthroses or amphiarthroses, include particularly cartilaginous bone connections. These include synchrondroses, which ensure a connection via hyaline cartilage (e.g. costal cartilage) or symphyses, which mean connection via fibrocartilage (e.g. intervertebral discs). But also connective tissue bone connections, such as seams between the skull bones or syndemoses as a ribbon-like connection between ulna and radius are examples of synarthrotic joints.

In diarthrotic (discontinuous) joints, also referred to diarthroses, there is usually a so-called joint gap between the ends of the bones, wherein the joint surfaces are covered by articular cartilage. There is a joint capsule around the joint, comprising an outer fibrous membrane (tight connective tissue) and an inner synovial membrane (an epithelial-like connective tissue association).

Collagenous connective tissue is used to stabilize diarthrotic, amphiarthrotic or synarthrotic joints. The collagenous connective tissue can lose its biomechanical properties through wear and tear or aging processes. This causes diseases which can be treated by administering riboflavin according to the invention.

The diseases that can be treated thus relate particularly to disorders of the biomechanical function of collagenous tissue in the joints, for example a reduction in elasticity due to age or wear.

The claimed riboflavin is preferably characterized in that it is administered in situ in the patient to a collagenous tissue of the joint, followed by UV irradiation.

Local administration can be performed in a number of ways. For example, drops of a riboflavin solution can be applied in situ to the relevant site, such that the riboflavin diffuses into the underlying tissue layers. In addition to such an instillation, it can also be preferred that the riboflavin is injected locally into the collagenous tissue of the diseased joint.

The riboflavin spreads through diffusion in the collagenous tissue of the joint, such that, depending on administration and concentration, it is largely homogeneous within a few minutes.

For photopolymerization and crosslinking of the collagen fibers, the affected tissue is irradiated with electromagnetic radiation in situ after administration of the riboflavin. Electromagnetic radiation is preferably understood to mean light which can include both visible light and invisible light, particularly ultraviolet (UV) light, or infrared (IR) light as well.

In preferred embodiments, the electromagnetic radiation is in a wavelength range from 200 nm to 3000 nm, preferably from 200 nm to 1500 nm. Any wavelength range which induces a riboflavin-mediated photopolymerization of the collagen fibers can preferably be used. For this purpose, for example, both UV irradiation and multiphoton irradiation using non-linear optical effects are suitable.

In contrast to other approaches in the prior art, the crosslinking reaction can advantageously take place in a spatially and temporally controlled manner by means of electromagnetic radiation, for example by means of UV light or multiphoton excitation. The local administration of riboflavin together with local irradiation causes a twofold focus on a desired tissue area, such that any undesired collagen cross-links in adjacent tissue layers are effectively avoided. In addition, networking can take place within a short period of time. For example, adequate stabilization of the tissue can be achieved within a few minutes by means of UV irradiation or multiphoton irradiation.

Due to the local administration in-situ and subsequent irradiation, extraction of the collagenous tissue for ex-situ preparation and subsequent return is not necessary. This simplifies the therapy and also reduces the risk of a rejection reaction by the immune system or the occurrence of other side effects.

In a preferred embodiment, the electromagnetic radiation is UV radiation. UV radiation is preferably understood to mean radiation in a wavelength range of 200-400 nm, particularly preferably 320-380 nm.

The UV irradiation results in a detectable crosslinking of the collagen fibers in the tissue of an affected joint, particularly an intervertebral disc, on which there is a sufficient concentration of riboflavin. FIG. 1 shows various molecular mechanisms which play a role here.

In another preferred embodiment of the invention, the irradiation takes place at a wavelength of more than 700 nm, wherein a pulsed light source is preferably used, such that a crosslinking reaction mediated by riboflavin is preferably brought about by non-linear optical effects.

The non-linear optics (NLO) or non-linear optical effects preferably designate the interaction of electromagnetic waves in which the relationship between the electric field and electric polarization in a medium is not linear, but rather of a higher degree. In the field of non-linear optics, it is particularly known that two or more photons can be absorbed simultaneously by a molecule or an atom, which as a result changes into an energetically excited state. The process is also known as multiphoton excitation or multiphoton absorption.

If a molecule such as riboflavin can be excited, for example, in the area of linear optics (i.e. with simultaneous absorption of one photon per molecule) by means of UV light having a wavelength of 370 nm, two-photon absorption with light of essentially double the wavelength, i.e. 740 nm, can occur. Non-linear optical effects only occur at very high intensities. Polarization for low intensities approximately increases linearly with the electric field, with electric susceptibility as the proportionality factor. In other words, one-photon absorption has a linear dependence on the intensity of the light.

In the case of two-photon absorption, on the other hand, two photons must be absorbed simultaneously, such that there is a squared dependence on the intensity of the light: In other words, to describe the relationship between polarization and electric field, higher-order terms must be taken into account for the electrical susceptibility. For a two-photon absorption this corresponds to a square order, while for a 3-photon absorption process the cubic order of the electrical susceptibility characterizes the absorption probability.

In order to provide high intensities, which are necessary for multiphoton processes, there is preferably a pulsed radiation, i.e. an irradiation which is characterized by a sequence of light pulses.

Pulse lasers are particularly suitable for pulsed radiation for non-linear excitation. Unlike continuous wave lasers (CW lasers), pulsed lasers do not emit light continuously, but in pulsed form. This means that the light is emitted in a sequence of light pulses. A distinction is made based on the duration of the pulses, for example, between nanosecond, picosecond and, particularly, femtosecond lasers.

Using a femtosecond laser (wavelength=760 nm), for example, very good results could be achieved for a riboflavin-mediated crosslinking of collagen tissues. The various molecular mechanisms by which riboflavin induces the crosslinking of collagen tissues can partly take place analogously to the mechanisms shown in FIG. 1, but excitation does not occur with UV light but, for example, with pulsed lasers having a wavelength of 700 nm or more.

Multiphoton irradiation for photoactivation has a number of particular advantages over UV irradiation. Particularly, the risk of cell damage, for example of the DNA from UV radiation or the occurrence of oxygen-free radicals, can be avoided through multiphoton irradiation. Furthermore, multiphoton excitation enables very precise irradiation. As explained above, a two-photon excitation, for example, depends on the square of the intensity, such that it is intrinsically guaranteed that the non-linear optical effects and therefore crosslinking takes place in a targeted manner in very small volumes.

Another decisive advantage is the option of using low-energy, long-wave light, for example having a wavelength of 700 nm or more. While short-wave UV light is severely scattered or absorbed by human tissue and can only reach shallow tissue depths, low-energy, long-wave light with wavelengths of 700 nm or more can penetrate several millimeters into the tissue structures.

Instead of a crosslinking reaction on the surface, a crosslinking reaction of the collagen fibers can be catalyzed with high precision, both laterally and axially, even in deep tissue structures.

The inventors have detected that the aforementioned advantages are transferred to a particular extent to the improvement of the treatment options for diseases of diarthrotic, amphiarthrotic or synarthrotic joints. Not only can photopolymerization take place in-situ in a more focused manner in deep tissue layers. In addition, undesired cell damage in these particularly sensitive tissue structures can also be avoided. According to the invention, riboflavin can particularly preferably be used for the treatment of intervertebral disc diseases.

In another aspect, the invention therefore relates to riboflavin for use as a medicament in the treatment of a patient with an intervertebral disc disease, wherein the treatment comprises local administration of riboflavin at the site of the disease of the intervertebral disc and subsequent irradiation of the site of the disease.

The location of the disorder of the intervertebral disc preferably means a location of the intervertebral disc which has undergone at least partial degeneration.

For example, the intervertebral disc disease to be treated can be a herniated disc, wherein parts of the nucleus pulposus that has emerged into the spinal canal are surgically removed at the site of the disease. By means of local administration of riboflavin, the remaining tissue of the intervertebral disc is strengthened in the affected area, such that a new intervertebral disc herniation is effectively prevented.

In the case of intervertebral disc protrusion or disc prolapse, the nucleus pulposus bends into the spinal canal, but does not yet exit it. The annulus fibrosus is largely intact and prevents leakage. However, in this case too, local administration of riboflavin can advantageously strengthen the degenerated intervertebral disc tissue in such a way that the protrusion recedes or at least does not advance any further.

The riboflavin that can be administered according to the invention can, however, also be used to strengthen degenerated intervertebral disc tissue before an exit or bulging of the nucleus pulposus into the spinal canal becomes visible.

For example, an intervertebral disc can lose its elasticity due to insufficient supply of the chondrocytes of the nucleus pulposus or weakening of the concentric tissue layers of the annulus fibrosus. The diseased area of the intervertebral disc does not yet emerge into the spinal canal, but due to the reduced biomechanical stability it can already lead to back problems or represent an increased risk. In this case as well, the claimed local administration of riboflavin can stabilize the tissue again.

Local administration can be performed in a number of ways. For example, drops of a riboflavin solution can be applied in situ to the relevant site, such that the riboflavin diffuses into the underlying tissue layers. In addition to such an instillation, it can also be preferred that the riboflavin is injected locally into the tissue layers of the intervertebral disc.

After local administration, the riboflavin shows a diffusion behavior, which allows an optimal cross-linking of the intervertebral disc tissue. This could not be expected from previous applications in the treatment of keratoconus.

Depending on administration and concentration, the riboflavin spreads homogeneously in the tissue of the nucleus pulposus and the annulus fibrosus within seconds to a few minutes. This is advantageously done without excessive dilution by diffusion into adjacent tissue layers. Instead, the riboflavin can be introduced into the diseased area of the intervertebral disc tissue in a controlled manner through local administration in order to strengthen the tissue in situ through photopolymerization.

For this purpose, after local administration of the riboflavin, the relevant site is locally irradiated with electromagnetic radiation, for example UV light or a pulsed laser having a wavelength of 700 nm or more. This locally supports the establishment of cross-links between the collagen fibers in a controlled manner, such that the biomechanical support function of the intervertebral disc is restored.

It is particularly surprising, however, that the irradiation not only strengthens the individual intervertebral disc components, but also stabilizes the connection between the nucleus pulposus and the surrounding annulus fibrosus.

Since the biomechanical elasticity of the intervertebral disc depends on the interaction of both tissues, the cross-linking mediated by the riboflavin leads to particularly good results. In contrast to prior art approaches in which a hydrogel is transplanted into the nucleus pulposus, the administration of the riboflavin according to the invention can thus achieve an improved overall stabilization of the intervertebral disc system.

In addition, cross-linking by riboflavin increases the fatigue resistance of the treated tissue, reduces degeneration resulting from repeated physiological stress, increases the resistance to potential rupture of the annulus fibrosus and the hydraulic permeability of the nucleus pulposus.

In another embodiment, the invention relates to a riboflavin for use as a medicament in the treatment of a patient with a deformation of the spine, particularly a spondylolisthesis or scoliosis.

Spondylolisthesis designates an instability of the spine in which the upper part of the spine slides with the gliding vertebra over the vertebral body below. The vertebral joints can be stabilized by local administration of riboflavin and subsequent crosslinking by irradiation, so that sliding is prevented. It can also be used prophylactically in order to prevent such diseases through constant stabilization of the spine.

Scoliosis is a lateral deviation of the spine from the longitudinal axis, possibly with rotation of the vertebrae and torsion of the vertebral bodies, which can also be accompanied by structural deformations of the vertebral bodies. Targeted local strengthening of collagenous tissues, which connect and support the bony vertebrae, can reduce lateral deviation and the associated symptoms.

In another embodiment, the invention relates to a riboflavin for use as a medicament in the treatment of a disease of a diarthrotic joint. Diarthrotic joints, such as knees, elbows, shoulders, etc. are also exposed to high pressure loads and physiological aging processes, which can lead to signs of wear and tear or functional disorders. Riboflavin can also advantageously be used for such diseases in order to strengthen a collagenous connective tissue, for example in a joint capsule.

In a preferred embodiment, the invention relates to a riboflavin for use as a medicament in the treatment of a patient with an intervertebral disc disease, wherein the local administration comprises an injection of the riboflavin, preferably into the annulus fibrosus and/or the nucleus pulposus.

Compared to other local administrations, such as instillation, the injection is characterized by a particularly controllable diffusion behavior of the riboflavin in the affected tissue. The injection already breaks through a physical barrier, preferably at least the outer layer of the annulus fibrosus, such that the diffusion inside the intervertebral disc is faster and more homogeneous. The injection can be given, for example, by means of a syringe with an attached cannula. However, other medical injection media can also be used for this purpose.

In another preferred embodiment, the invention relates to a riboflavin for use as a medicament in the treatment of a patient with an intervertebral disc disease, wherein the local administration comprises an injection of the riboflavin, preferably into the annulus fibrosus and/or the nucleus pulposus. This form of administration is therefore preferably a double injection, both into the annulus fibrosus and into the nucleus pulposus.

On the one hand, this shortens the diffusion time for the riboflavin to spread completely in the desired intervertebral disc area. On the other hand, there is a surprisingly stable crosslinking of the two tissue components of the intervertebral disc and excellent restoration of the elasticity of the degenerated tissue section. The advantageous diffusion profile also develops with lower doses of riboflavin, such that the total dose can be reduced.

In another preferred embodiment, the invention relates to a riboflavin for use as a medicament in the treatment of a disease of a diarthrotic, amphiarthrotic or synarthrotic joint, preferably a disc disease, wherein the irradiation is UV irradiation and is performed at a wavelength between 200 and 400 nm, preferably between 320 and 380 nm and/or a radiation intensity of 0.1 mW to 500 mW, preferably 0.2 to 50 mW.

The aforementioned parameters have proven to be particularly advantageous experimentally. In this way, excellent results are achieved with regard to the crosslinking capacity and the resulting structure of an elastic fabric. Despite the reliable photopolymerization, only the necessary energy transfer into the tissue takes place with the aforementioned parameters. Radiation-based side effects can be effectively avoided.

In another preferred embodiment, the invention relates to a riboflavin for use as a medicament in the treatment of a disease of a diarthrotic, amphiarthrotic or synarthrotic joint, preferably an intervertebral disc disease, wherein the irradiation is performed with pulses at a wavelength of more than 700 nm and a pulse duration in the nanosecond or femtosecond range.

Nanosecond range preferably means a range from 1 ns (nanosecond) to 1000 ns. Femtosecond range preferably means a range from 1 fs (femtosecond) to 1000 fs.

In a preferred embodiment, the pulse duration is in the range from 10 fs to 500 fs, particularly preferably 50 fs to 250 fs. Intermediate ranges from the aforementioned ranges can also be preferred, such as 10 fs to 50 fs, 50 fs to 100 fs, 100 fs to 150 fs, 150 fs to 200 fs, 200 fs to 250 fs, 250 fs to 300 fs, 300 fs up to 350 fs, 350 fs to 400 fs, 400 fs to 450 fs, or even 450 fs to 500 fs. A person skilled in the art recognizes that the aforementioned range limits can also be combined in order to obtain other preferred ranges, such as, for example, 10 fs to 150 fs or 200 fs to 250 fs.

In a preferred embodiment, the wavelength of the pulses is in the range from 700 nm to 820 nm, particularly preferably 720 nm to 800 nm, most preferably 740 nm to 780 nm. Intermediate ranges from the aforementioned ranges can also be preferred, such as 700 nm to 720 nm, 720 nm to 740 nm, 740 nm to 760 nm, 760 nm to 780 nm, 780 nm to 800 nm, or 800 nm to 820 nm. A person skilled in the art recognizes that the aforementioned range limits can also be combined in order to obtain other preferred ranges, such as, for example, 700 nm to 760 nm or 720 nm to 800 nm.

In one embodiment, the repetition rate of the pulses is in a range from 10 MHz to 100 MHz and/or the energy per pulse is 1 nJ to 1 μJ (joule), preferably 1 nJ to 100 nJ.

Typical commercially available titanium-sapphire lasers (see, inter alia, the Chameleon product range (e.g. Chameleon Ultra) from Coherent Inc., Santa Clara) have, for example, a repetition rate of 70 to 90 MHz in modelock operation with pulse energies in the range of a few nanojoules. The disadvantage of the high repetition rates is their high average radiation intensity.

In a preferred embodiment, the repetition rate of the light pulses is in a range from 1 kHz to 1000 kHz, preferably 1 kHz to 100 kHz, particularly preferably 1 kHz to 50 kHz, and/or the energy per pulse is 100 nJ to 50 μJ (joule), preferably 0.5 μJ to 5 μJ.

With regard to the repetition rate, intermediate ranges from the aforementioned ranges can also be preferred, such as, for example, 1 kHz to 5 kHz, 5 kHz to 10 kHz, 10 kHz to 20 kHz, 20 kHz to 50 kHz, 50 kHz to 100 kHz, 100 kHz to 200 kHz, 200 kHz to 500 kHz, or 500 kHz to 1000 kHz. A person skilled in the art recognizes that the aforementioned range limits can also be combined in order to obtain other preferred ranges, such as, for example, 5 kHz to 20 kHz or 10 kHz to 50 kHz.

Intermediate ranges can also be preferred with regard to the energy per pulse, such as 100 nJ to 200 nJ, 200 nJ to 500 nJ, 500 nJ to 1 μJ, 1 μJ to 2 μJ, 2 μJ to 5 μJ, 5 μJ to 10 μJ, 10 μJ to 20 μJ or 20 μJ to 50 μJ. A person skilled in the art recognizes that the aforementioned range limits can also be combined in order to obtain other preferred ranges, such as, for example, 200 nJ to 2 μJ or 1 μJ to 20 μJ.

In the prior art, it is known to amplify the pulses of a femtosecond laser (e.g. Ti:Sa) with a repetition rate of 70 to 90 MHz and pulses in the nanojoule range to repetition rates in the kHz range and energy pulses in the range of 0 (microjoules) or mJ (millijoules) by means of regenerative amplification or chirped pulse amplification, for example. While such amplification techniques are preferably used to generate very powerful laser pulses (see Dubietis et al. 2006), in the context of tissue radiation, the average radiation intensity and thus the thermal load on the tissue can be kept particularly low.

As Samantha et al 2017 were able to show in relation to the cornea, for example, a riboflavin-mediated crosslinking of the collagen fibers can take place at a repetition rate of 76 MHz and a pulse energy of 11 nJ/pulse, wherein the average radiation intensity is 900 mW. Likewise, a riboflavin-mediated crosslinking of the collagen fibers can be performed at a repetition rate of 5 kHz and a pulse energy of 2.4 μJ/pulse, wherein the average radiation intensity is just 12 mW.

In a preferred embodiment, the average radiation intensity for the irradiation with light pulses is in the range from 0.1 mW to 1000 mW, preferably 0.2 to 100 mW, particularly preferably 1 mW to 50 mW. The parameters mentioned above are particularly advantageous in order to ensure a high degree of crosslinking with precise control even in deeper tissue layers. In another preferred embodiment, the invention relates to riboflavin for use as a medicament in the treatment of a disease of a diarthrotic, amphiarthrotic or synarthrotic joint, preferably an intervertebral disc disease, wherein the UV irradiation is started after a period of 10 sec (seconds) to 30 min, preferably 30 sec to 20 min, after the local administration of the riboflavin and takes place for a period of 10 seconds to 30 minutes, preferably 30 seconds to 10 minutes.

The best therapeutic results are recorded when the specified time sequence and time periods are used. On the one hand, the periods of time are sufficient to ensure a sufficiently homogeneous distribution of the riboflavin over the desired area. On the other hand, the upper limits can prevent the riboflavin from already diffusing to a significant extent into adjacent tissue layers. With a low dosage of riboflavin, this ensures excellent crosslinking of the collagen tissue without crosslinking reactions occurring in possibly undesired areas.

In another aspect, the invention relates to a pharmaceutical composition for use as a medicament in the treatment of a patient with a disease of a synarthrotic, diarthrotic or amphiarthrotic joint, preferably an intervertebral disc disease, as described herein, comprising a) a riboflavin according to the invention or a preferred embodiment thereof b) a pharmaceutical carrier The pharmaceutical carrier preferably relates to a material, particularly preferably in liquid form as a solution, which does not interfere with the action of the riboflavin. Instead, the pharmaceutical carrier preferably serves both to stabilize the riboflavin for storage and to effectively administer it to the tissue in question. Various pharmaceutical carriers can preferably be used for this purpose and contain, for example, water, salts, buffer substances, or preservatives.

In a particularly preferred embodiment, the pharmaceutical carrier is a hypoosmolar solution. The term hypoosmolar preferably means that the solution has a lower osmolarity than the liquid in the collagenous connective tissue in which the riboflavin is administered locally. Osmolarities of 1 mOsm/L to 2000 mOsm/L are particularly preferred, the osmolarity or the osmotic concentration indicating the molar concentration (or molarity) of the osmotically active particles in the solution.

With a hypoosmolar solution, particularly good results can be achieved with respect to the spatial-temporal spread of the pharmaceutical composition in the tissue concerned. Particularly, the hypoosmolar solution ensures that the active ingredient riboflavin reliably penetrates the collagen-containing connective tissue, such as the nucleus pulpusus or the annulus fibrosus, and leads to reinforcement of the collagen fibers after UV radiation.

In another preferred embodiment, the invention relates to a pharmaceutical composition for use as a medicament in the treatment of a patient with a disease of a diarthrotic, amphiarthrotic or synarthrotic joint, preferably an intervertebral disc disease, wherein the riboflavin is present in the pharmaceutical composition at a concentration of 0.01% by weight to 5% by weight.

Intermediate ranges can also be preferred from the aforementioned ranges, such as 0.01% by weight to 0.05% by weight, 0.05% by weight to 0.1% by weight, 0.1% by weight, for example. % to 0.2% by weight, 0.2% by weight to 0.5% by weight, 0.5% by weight to 1% by weight, 1% by weight to 2% by weight, 2% by weight to 5% by weight, 0.01% by weight to 5% by weight, 0.01% by weight to 5% by weight, 0.01% by weight to 5% by weight. A person skilled in the art recognizes that the aforementioned range limits can also be combined in order to obtain other preferred ranges, such as, for example, 0.5% by weight bis 2% by weight or 0.2% by weight to 2% by weight.

The aforementioned concentrations can be used to achieve optimal results with regard to a homogeneous distribution of the active ingredient in the desired tissue area, particularly in an aqueous solution, preferably a hypoosmolar solution. The concentration is low enough to avoid undesirable side effects or clumping in the tissue, but high enough to achieve an effective therapeutic effect.

The amount of the administered pharmaceutical composition can be adjusted individually to factors such as the degree of the disease or the size of the collagenous tissue.

If parts of the nucleus pulposus have been surgically removed in the case of a disc disease, the remaining cavity can be completely filled with the pharmaceutical composition. In the case of an injection into the annulus fibrosus or nucleus pulposus to strengthen the intervertebral disc tissue, volumes of 0.01 ml to 10 ml prove to be particularly suitable.

Intermediate ranges from the aforementioned ranges can also be preferred, such as 0.01 mL to 0.05 mL, 0.05 mL to 0.1 mL, 0.1 mL to 0.5 mL, 0.5 mL to 1 mL, 1 mL to 5 mL, 5 mL to 10 mL. A person skilled in the art recognizes that the aforementioned range limits can also be combined in order to obtain other preferred ranges, such as, for example, 0.5 mL to 5 mL or 0.01 mL to 1 mL.

In another aspect, the invention relates to a method for treating a patient with an intervertebral disc disease comprising the steps

- provision of riboflavin or a pharmaceutical composition for use as a medicament in the treatment of a patient with a disease of a synarthrotic, diarthrotic or amphiarthrotic joint, preferably an intervertebral disc disease, as described herein, comprising
- local administration of riboflavin into a collagenous tissue of the joint
- irradiation of the collagenous tissue.

A person skilled in the art recognizes that preferred embodiments and advantages which have been disclosed for the riboflavin for use as a medicament apply likewise to the method. For example, a local injection into the nucleus pulposus and/or the annulus fibrosus has been disclosed as the preferred administration for riboflavin. Such an injection is therefore equally preferred for the method.

In another aspect, the invention relates to a kit for treating a patient with an intervertebral disc disease comprising

- riboflavin or a pharmaceutical composition for use as a medicament in the treatment of a patient with a disease of a amphiarthrotic, synarthrotic or diarthrotic joint, preferably an intervertebral disc disease, as described herein, comprising
- an injection device suitable for injection into the intervertebral disc
- a radiation device and, optionally, instructions for the treatment of a patient in situ by local administration of riboflavin in a collagenous tissue of the joint and subsequent exposure to electromagnetic radiation, preferably UV radiation or multiphoton radiation with a wavelength of 700 nm or more.

A person skilled in the art recognizes that preferred embodiments and advantages which have been disclosed for the riboflavin or the pharmaceutical composition for use as a medicament apply likewise to the kit. For example, a hypoosmolar solution has been disclosed as the preferred pharmaceutical carrier for the pharmaceutical composition. Likewise, it is also preferred in the kit to have riboflavin in dissolved form in a hypoosmolar solution.

The instructions optionally contained in the kit also include preferred embodiments of the described method for treating the disease of the joints, preferably the intervertebral disc.

As an injection device for the kit, any device is suitable which has the dimensions and design to inject a pharmaceutical composition into a collagenous tissue of a joint, preferably an intervertebral disc. The injection device will therefore preferably comprise a reservoir for a pharmaceutical composition and an injection tip which is suitable for penetrating into a collagenous tissue. For example, a syringe with a cannula can preferably be used as an attachment.

An irradiation device is preferably understood to mean a device which is capable of emitting electromagnetic radiation with the preferred parameters described.

In a preferred embodiment, the irradiation device is a UV irradiation device.

A UV irradiation device is preferably understood to mean a device which is capable of emitting UV radiation with the in the range from 200-400 nm. Various devices for this purpose are known in the prior art. For example, LEDs with radiation in the UV range can be used.

In a preferred embodiment, the irradiation device is a pulse laser for generating light pulses at a wavelength of 700 nm or more. Various devices for this purpose are known in the prior art. For example, Ti:Sa femtosecond lasers can optionally be used with an additional amplification for the desired setting of the repetition rate and/or pulse energies (see above).

A combination of an irradiation device, an injection device for a collagenous tissue of a joint and riboflavin provided according to the kit is not known in the prior art, particularly not in connection with instructions for performing in-situ crosslinking.

DETAILED DESCRIPTION

The invention relates to riboflavin or a pharmaceutical composition for use as a medicament in the treatment of diseases of amphiarthrotic, synarthrotic or diarthrotic joints, preferably for the treatment of intervertebral disc diseases.

The "use of a drug to treat" a subject or patient suffering from a disease preferably means slowing, halting, or reversing the progression of the disease.

In the preferred embodiment, the use of a medicament in treating a patient means reversing the progression of the disease, ideally to a point where the disease itself is cleared.

Improving the symptoms of the disease or eliminating the causes of such a disease can also fall under the term of treatment. The treatment can also alternatively relate to prophylactic administration of the active ingredients described herein. Such prophylactic administration may refer to the prevention of a medical disease or the prevention of the development of such a disease, the terms prevention and prophylaxis are not to be interpreted narrowly. Prevention or prophylaxis can also refer to reducing the risk that a subject or patient will develop a disease, preferably in a subject or patient at risk for this condition.

"Riboflavin" is also known as lactoflavin or vitamin B2 in the prior art and is chemically referred to as 7,8-dimethyl-10-(D-ribo-2,3,4,5-tetrahydroxypentyl)-3H,10H-benzo [g]pteridine-2,4-according to IUPAC or as 7,8-dimethyl-10-(D-ribit-1-yl)-isoalloxazine according to WHO. Other chemical terms herein are used in accordance with conventional usage in the field as explained by The Mc-Graw-Hill Dictionary of Chemical Terms (Parker, S., eds., McGraw-Rill, San Francisco (1985)), which is incorporated herein by reference.

However, the term riboflavin is also intended to cover functional equivalents or analogs which continue to have the desired biological activity, i.e., catalysis for crosslinking collagen tissues when exposed to UV radiation.

Functional equivalence is given, particularly, if under otherwise comparable conditions, a degree of crosslinking of collagen tissues of about 10%, 20%, 30%, 40% or 50%, preferably 60%, 70%, 80%, or 90%, particularly preferably 100%, 125%, 150%, very particularly preferably 200%, 300%, or 400%, most preferably 500%, 600%, 700%, or 1000% is achieved compared to the quantitative tests described in the examples.

Particularly, the term riboflavin should therefore also include isomers or derivatives of the above-mentioned chemical compound, as long as these are functionally equivalent.

An effective amount of the administered riboflavin or the pharmaceutical composition comprising the riboflavin is of the condition to be treated, the severity of the disease, the individual parameters of the patient, including age, physiological condition, height and weight, the duration of the treatment, the type of an accompanying therapy (if any), the specific route of administration, and similar factors.

The pharmaceutical compositions comprising riboflavin are preferably sterile and contain an effective amount of the therapeutically active substance for producing the desired reaction or effect.

The doses of the compositions according to the invention which are administered can depend on various parameters such as the mode of administration, the condition of the patient, the desired period of administration, and the like. In the event that a patient's response is inadequate at an initial dose, higher doses (or effectively higher doses obtained by a different, more localized route of administration) can be employed.

In general, amounts of riboflavin between 0.1 ng to 1000 mg, preferably 0.1 ng to 100 ng, 0.1 ng to 10 ng, 0.1 ng to 1 ng are used for treating diseases of diarthrotic, amphiarthrotic or synarthrotic joints, preferably intervertebral disc diseases, 1 ng to 1 mg, 1 ng to 100 ng, or 1 ng to 10 ng.

The pharmaceutical compositions are generally administered in pharmaceutically acceptable amounts and in pharmaceutically acceptable compositions.

The term "pharmaceutically acceptable" preferably relates to a non-toxic material which does not interfere with the action of the active ingredient of the pharmaceutical composition, preferably riboflavin.

Such preparations can usually contain salts, buffer substances, preservatives, carriers, and optionally other therapeutically active substances. When used in medicine, the salts should be pharmaceutically acceptable. However, non-pharmaceutically acceptable salts can be used in the preparation of pharmaceutically acceptable salts thereof and are included.

Such pharmacologically and pharmaceutically acceptable salts include in a non-limiting manner those which are prepared from the following acids: hydrochloric, hydrobromic, sulfuric, nitric, phosphoric, maleic, acetic, salicylic, citric, formic, malonic, succinic acid, and the like. Pharmaceutically acceptable salts can also be prepared as alkaline metal or alkaline earth metal salts such as sodium, potassium or calcium salts.

A pharmaceutical composition according to the invention can comprise a pharmaceutically acceptable carrier. The term "pharmaceutically acceptable carrier" preferably relates to one or more compatible solid or liquid fillers, diluents, or other substances which are suitable for administration to a human. The term "carrier" preferably relates to an organic or inorganic component, natural or synthetic in nature, in which the active component, preferably the riboflavin, is combined in order to facilitate use. The constituents of the pharmaceutical compositions are usually such that no interaction occurs which significantly impairs the desired pharmaceutical effectiveness.

The pharmaceutical compositions can contain suitable buffer substances such as acetic acid in a salt, citric acid in a salt, boric acid in a salt, and phosphoric acid in a salt.

The pharmaceutical compositions can also optionally contain suitable preservatives such as benzalkonium chloride, chlorobutanol, parabens and thimerosal.

The pharmaceutical compositions are usually presented in a unit dose form and can be prepared in a manner known as such.

Preferred pharmaceutically acceptable carriers include aqueous or non-aqueous solutions, suspensions and emulsions, most preferably aqueous solutions. Aqueous carriers include water, alcoholic or aqueous solutions, emulsions and suspensions, including saline and buffered media. Aqueous solutions include, particularly, sodium chloride solutions, Ringer's dextrose, dextrose, and sodium chloride, Ringer's lactate, and solid oils. Preservatives and other additives can also be present, such as antimicrobial agents, antioxidants, chelating agents, inert gases, and the like.

Local administration means that the riboflavin or the pharmaceutical administration into the collagenous tissue is preferably carried out in a spatially definable volume. Preferred local administrations include an injection or instillation into or onto the tissue in question. However, the local administration can also be administered in the vicinity of the tissue in question.

Local administration in the vicinity of the tissue in question includes, for example, local administration within 50 mm, 20 mm, 10 mm, 5 mm, within 1 mm of the tissue, within 0.5 mm of the tissue, and within 0.25 mm of the tissue.

The local administration of riboflavin or the pharmaceutical composition makes it possible to improve the therapeutic index, wherein any general toxicity and the risks of systemic effects are reduced overall.

The term "disease of diarthrotic, amphiarthrotic or synarthrotic joints" is understood to mean any disruption of the physiological function of the respective anatomical structures. This is preferably understood as a disease which is based on a disruption of the biomechanical stability of a collagenous tissue in the joint. In a healthy state, collagenous tissues stabilize various diarthrotic, amphiarthrotic or synarthrotic joints and thus support the connected skeletal structures or ensure their mobility.

The collagenous connective tissue can lose its biomechanical properties through wear and tear or aging processes. This causes diseases which can be treated by administering riboflavin according to the invention.

Such diseases include particularly diseases of diarthrotic joints, particularly of joint capsules, for example of knee, elbow, or shoulder joints, deformations of the spine, such as spondylolisthesis or scoliosis, or intervertebral disc diseases.

A collagenous tissue is preferably understood to mean any endogenous tissue of the human body which has collagen fibers in its natural state. Connective tissues are particularly preferred.

Collagen is a structural protein that occurs only in multicellular animals (including humans) and occurs mainly in connective tissues, especially in the extracellular matrix between the cells. Collagen is found, among other things, in the white, inelastic fibers of tendons, ligaments, bones, and cartilage and stabilizes both diarthrotic, amphiarthrotic and synarthrotic joints.

The collagen fibers, which are strong, but hardly stretchable, are 1 to 10 micrometers thick. In an electron microscope or in a fluorescence microscope, collagen fibers can be detected by their transverse stripes, which result from the overlapping arrangement of the collagen molecules during the synthesis of collagen fibrils.

A plurality of different types of collagen are found in the connective tissues. A total of 28 types of collagen (types I to XXVIII) are known, which can occur in different forms in the collagenous tissues. However, these are preferably collagen types I to IV.

One collagenous tissue which is particularly preferably treatable is the intervertebral disc, which particularly comprises the nucleus pulposus and annulus fibrosis.

Disc diseases are intended to include any medical condition that affects a disorder of the physiological function of the intervertebral disc. These include, but are not limited to, an intervertebral disc prolapse, an intervertebral disc protrusion, or a herniated disc.

FIGURES AND EXAMPLES

The invention is to be explained in more detail below on the basis of figures and examples, without being limited to these.

DETAILED DESCRIPTION OF THE FIGURES

Figure 1:
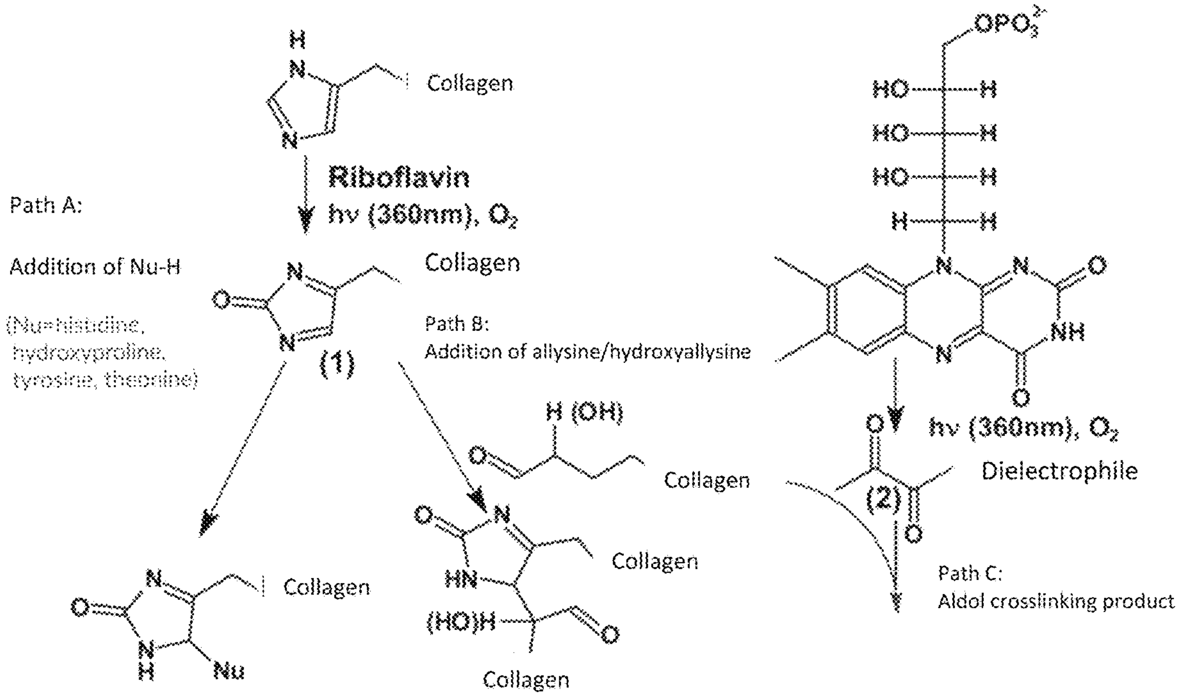
FIG. 1 Molecular mechanisms for the crosslinking of collagen molecules by riboflavin FIG. 2 Administration of riboflavin to the human cornea for the treatment of keratoconus FIG. 3 Collagen fibers before (left) and after (right) crosslinking by means of riboflavin FIG. 4 A schematic representation of the anatomical structure of an intervertebral disc FIG. 5 Preferred administration of riboflavin for the treatment of an intervertebral disc disease FIG. 6 Intervertebral disc of a bovine, wherein the annulus fibrosus (AF), the nucleus pulposus (NP) and a transition zone (rectangle) between AF and NP are marked FIG. 7 Samples of the transition zone between AF and NP of an intervertebral disc, as shown in FIG. 6, which were cut to 0.6 mm thin layers by means of a cryomicrotome.

FIG. 1 shows proposed mechanisms with which riboflavin can induce crosslinking of collagen molecules after UV irradiation. The reaction pathway (a) is oxygen dependent, whereby imidazolone (compound 1) is produced. This short-lived intermediate can react with an uncapped nucleophile (Nu). Reaction path (b) relates to endogenous carbonyl groups (allysines) as nucleophiles in an oxygen singlet-dependent byway. The reaction path (c) indicates that, when riboflavin is excited, a self-activation product of 2,3-butanedione riboflavin (compound 2) could be formed, which provides an additional oxygen singlet-dependent signaling pathway that reacts strongly with endogenous carbonyl groups (see McCall et al. 2010).

Figure 2:
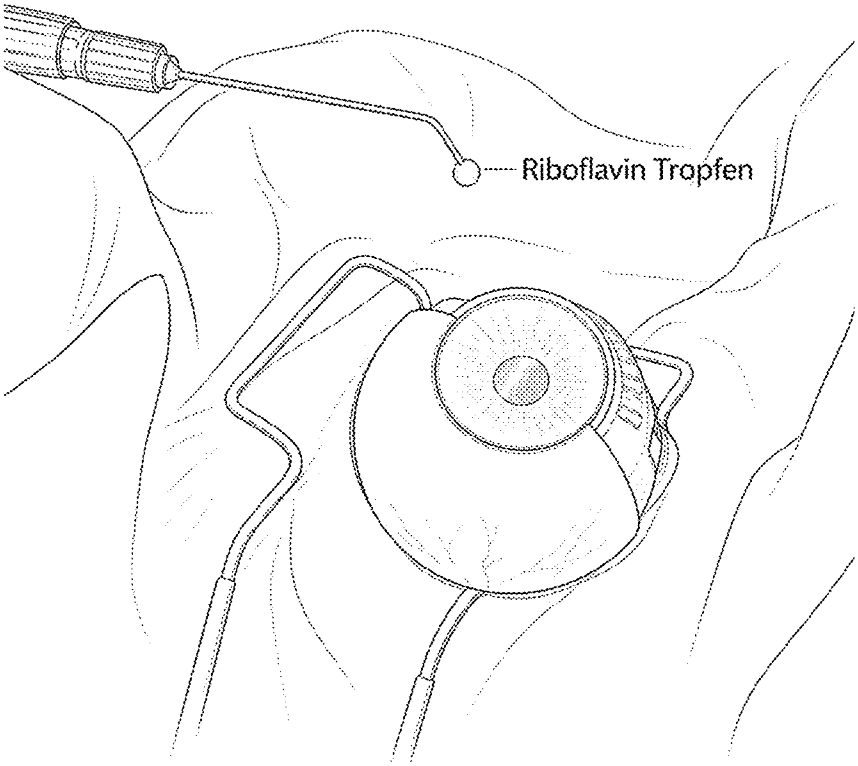

FIG. 2 shows a standard protocol for administering riboflavin to the human cornea for the treatment of keratoconus. Here, drops of a riboflavin solution are placed on the keratoconic cornea of the eye for a few minutes, such that the riboflavin can penetrate into the underlying tissue layers. The cornea is then irradiated with UV light at a wavelength of 360-370 nm at an intensity of 9 $mW/cm^2$ for 10 minutes.

Figure 3:
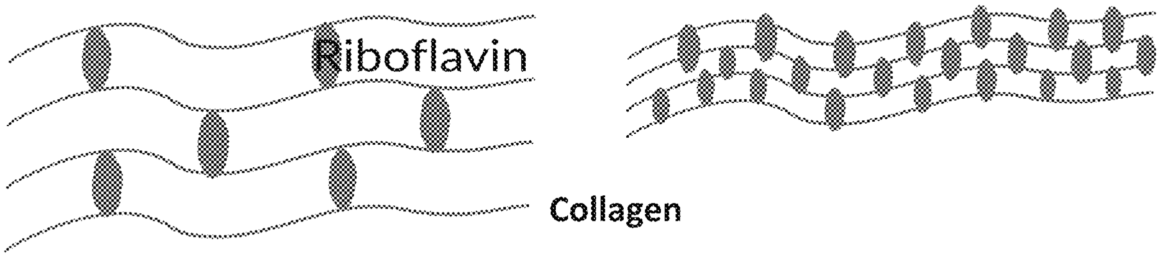

FIG. 3 schematically illustrates the collagen fibers before crosslinking (left) and after crosslinking (right).

Figure 4:
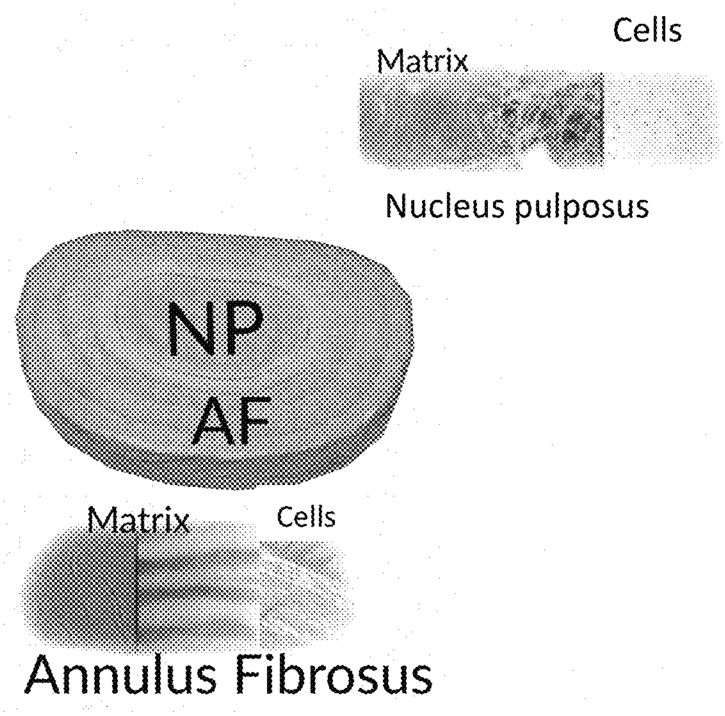

FIG. 4 is a schematic view of the anatomical structure of an intervertebral disc. The intervertebral disc is located between the vertebral bodies in the spine and is used to carry loads, ensure flexibility, and dissipate mechanical energy in the spine. The intervertebral disc consists of various anatomical zones: the annulus fibrosus (AF), the nucleus pulposus (NP), and the cartilage end plates. The annulus fibrosus (AF) consists of concentric lamellae with highly aligned collagen fibers, wherein the cells are typically aligned along the direction of the fibers. The nucleus pulposus is a gelatinous, highly hydrated tissue, with cells typically having rounded, unaligned morphologies. Images of the specific cell morphology in each region can be obtained by light microscopy.

Figure 5:
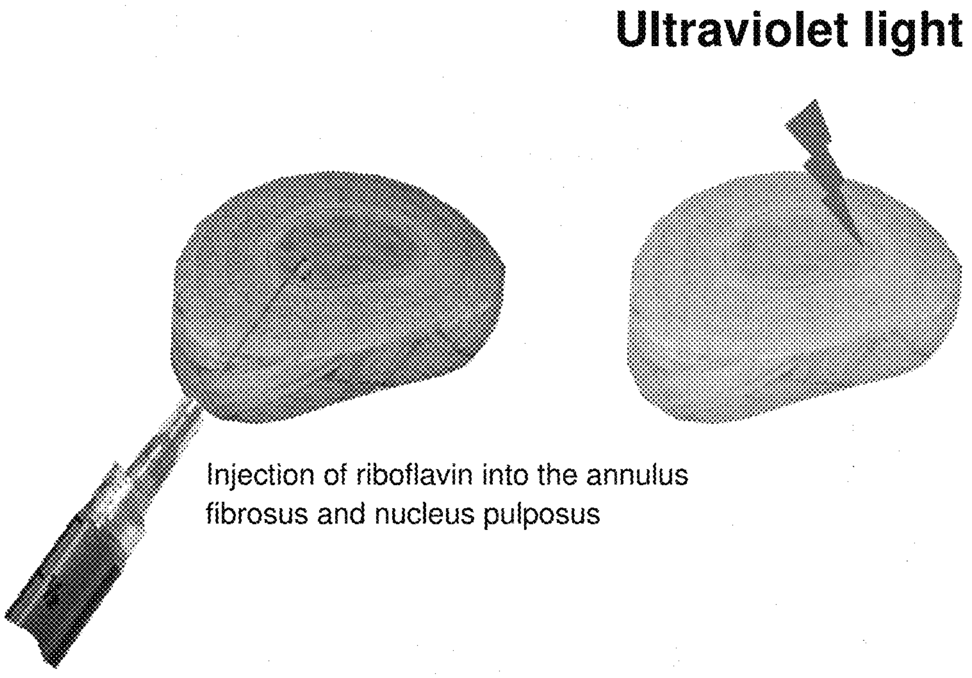

FIG. 5 shows a preferred administration of riboflavin for the treatment of an intervertebral disc disease. The riboflavin is injected in situ into the annulus fibrosus and/or the nucleus pulposus, particularly preferably one after the other into both tissues. The dose of the injection is adjusted in such a way that maximum effect (crosslinking) is achieved with minimum toxicity. The injection is followed by a pause, so that the riboflavin can distribute itself in the collagenous tissues on the basis of osmotic diffusion. This is followed by UV radiation in order to catalyze the crosslinking reaction between the collagen fibers.

The following experiments and examples show that riboflavin can be used to cross-link collagenous tissues in diarthrotic, amphiarthrotic or synarthrotic joints, especially in intervertebral discs, in order to increase their biomechanical stability.

Figure 6:
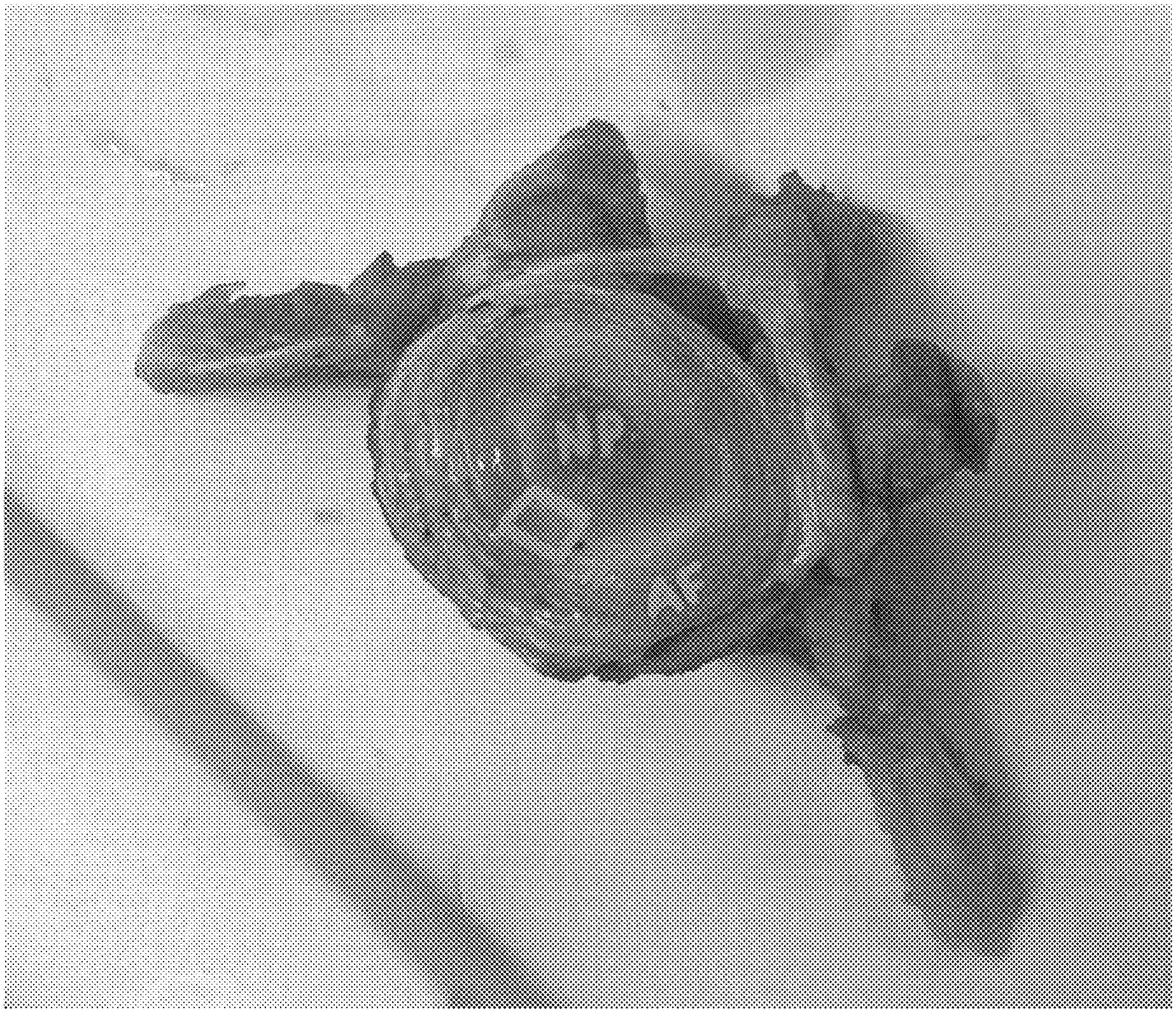

Five freshly frozen bovine intervertebral discs and two freshly frozen human intervertebral discs from the Anatomy department of the University of Freiburg were used for the experiments (see FIG. 6).

Figure 7:
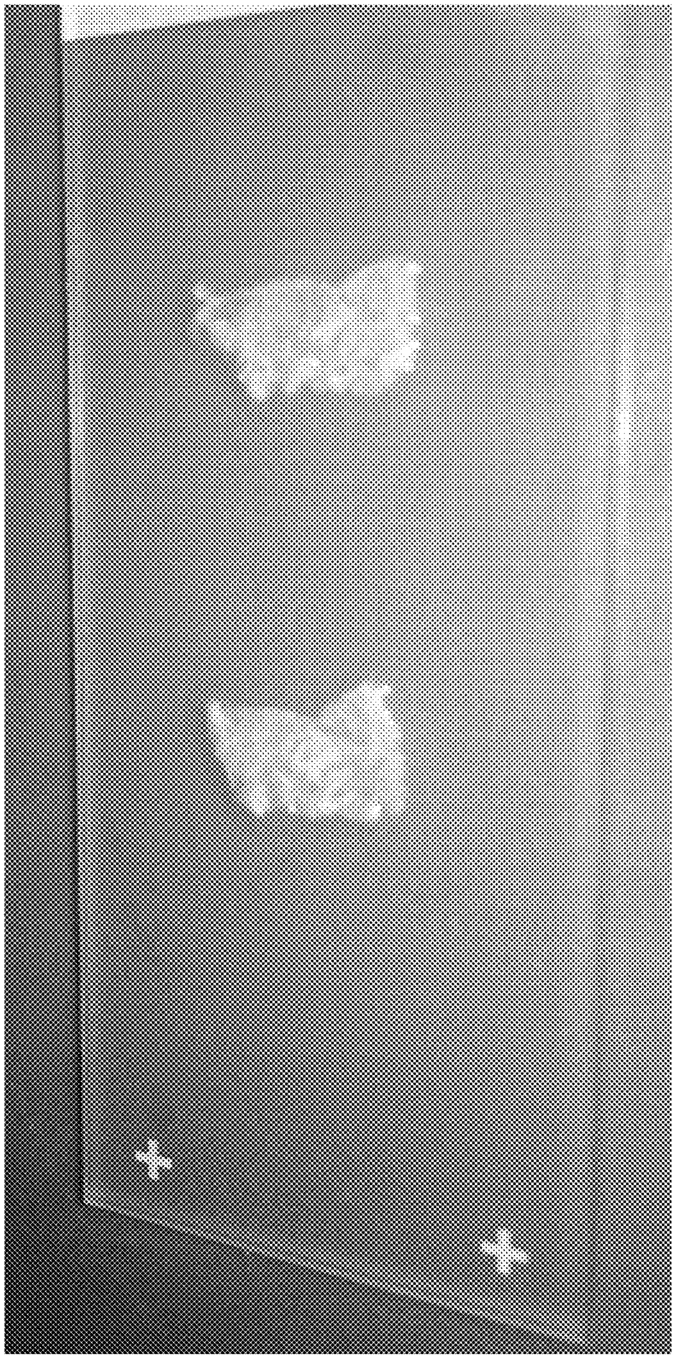

The intervertebral discs were thinly cut into 0.6 mm thick slices using a cryomicrotome and placed on glass plates (see FIG. 7). The thin discs arise from the transition zone between the annulus fibrosus and nucleus pulposus, which is indicated by a rectangle in FIG. 6.

A total of 10 bovine and 10 human samples were prepared and examined for the experiments.

Figure 9A:
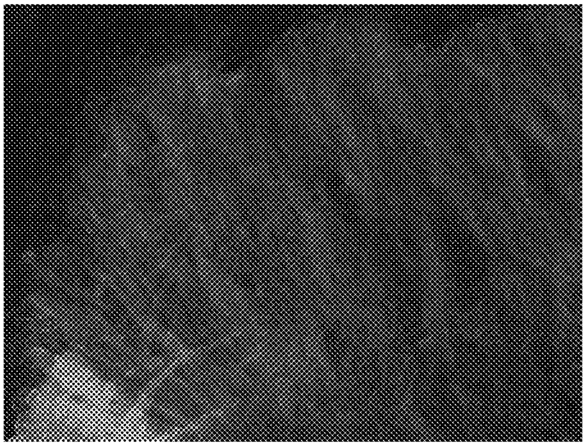
FIG. 9 Recording of the autofluorescence of a transition zone between AF and NP in a human intervertebral disc before a) and after b) the treatment with riboflavin and UV light FIG. 10 Recording of the autofluorescence of a transition zone between AF and NP in a human intervertebral disc before a) and after b) the treatment with riboflavin and UV light FIG. 11 Removal of paravertebral structures from bovine tails two hours after their slaughter FIG. 12 Isolation of bovine intervertebral discs attached to the vertebral body FIG. 13 Fixation of the vertebral bodies in bone cement (PMMA)
Figure 9B:
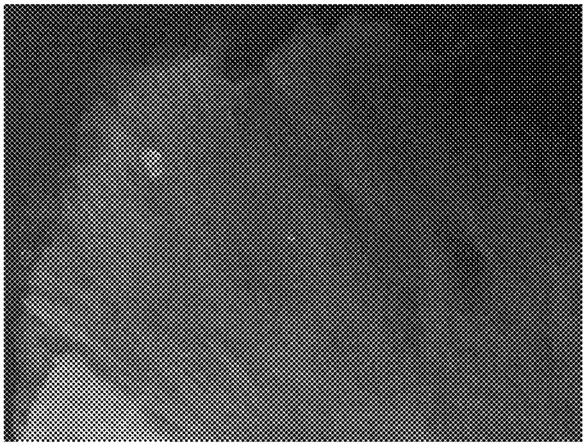
Figure 10A:
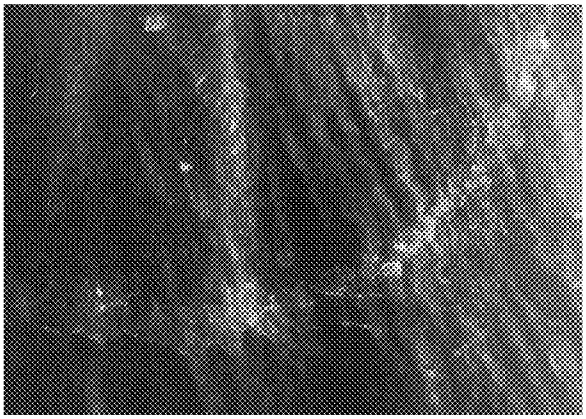
Figure 10B:
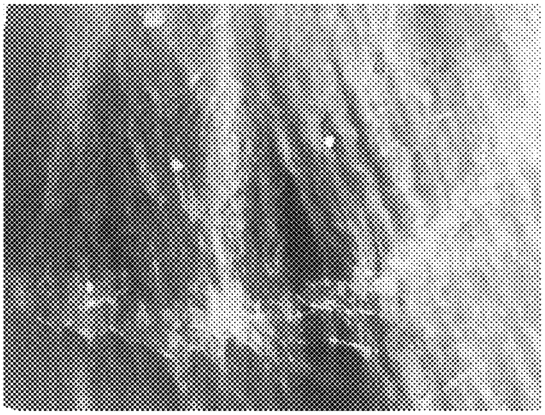

Before treatment with riboflavin, the samples were imaged by autofluorescence microscopy to visualize the collagen fibers. The architecture, orientation and crosslinking density of the collagen fibers in the samples before treatment are shown in FIGS. 9 *a*) and 10 *a*).

To crosslink the collagen fibers, 0.1 mL of a riboflavin solution at a concentration of 0.25% was administered twice at a time interval of 30 seconds. The sample was then irradiated with UV light.

Figure 8:
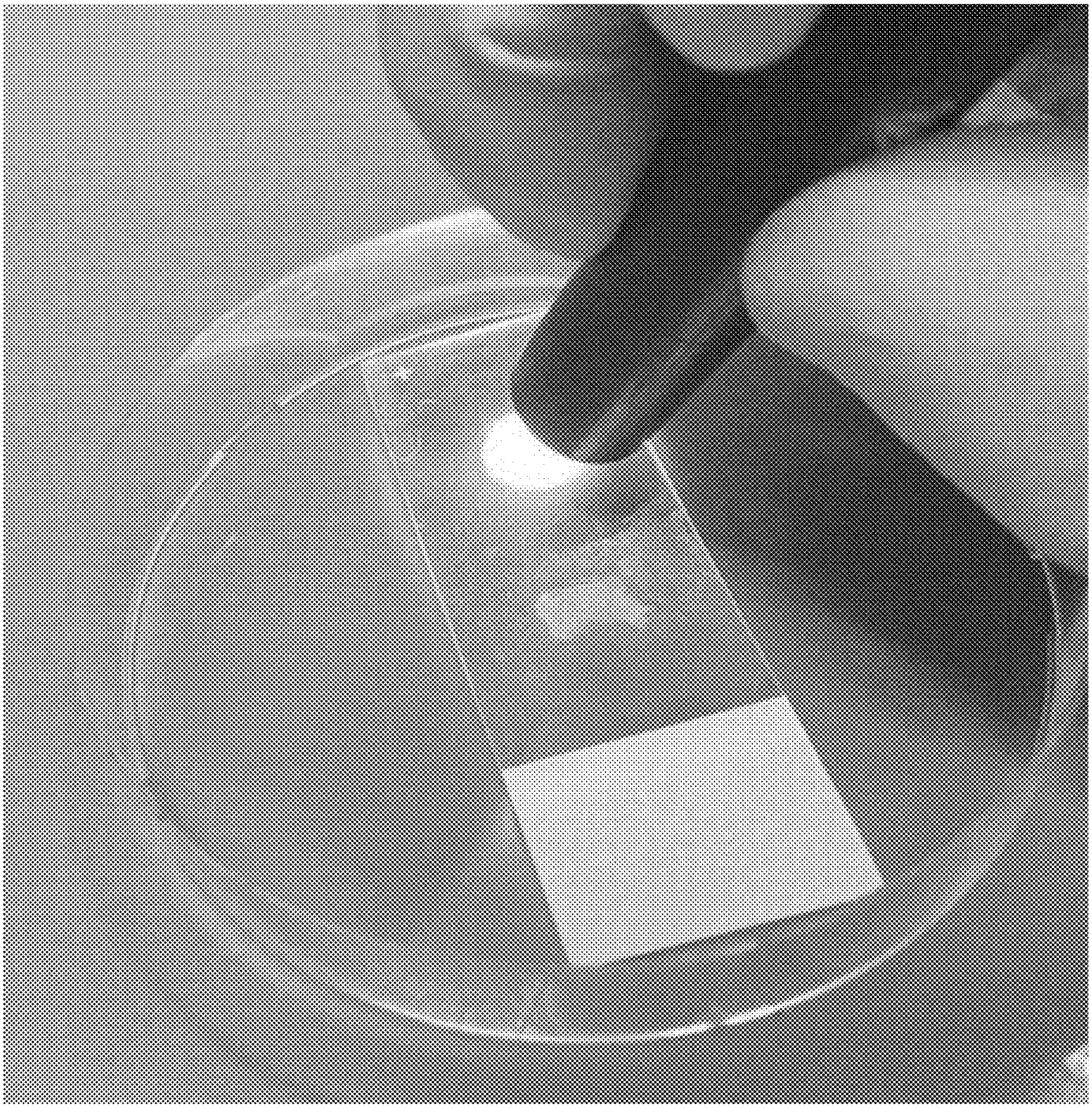
FIG. 8 UV irradiation after the addition of riboflavin

A UV radiation source with an average wavelength of 370 nm (365-375 nm) was used to irradiate the samples. The effective surface density of the intensity on the sample surface was calibrated to be 9 mW/cm$^2$, and the irradiation lasts two minutes (see FIG. 8).

After the treatment, the collagen fibers were reimaged using autofluorescence microscopy in order to visualize the identical sample area. This allows changes in the crosslinking density of the collagen fibers to be detected.

In all 20 related samples, treatment with the described protocol showed a visually evident increase in the crosslinking density in the transition zone between the annulus fibrosus and the nucleus pulposus. With an in-situ application, the stronger connection between the two tissues leads to an improved overall stabilization of the intervertebral disc.

The experiments described above verify the advantages of the therapeutic use of riboflavin particularly on the basis of thin cryosections of bovine and human intervertebral disc samples under direct microscopic visualization.

The following experiments demonstrate the beneficial biomechanical effects of the therapeutic use of riboflavin for fresh healthy bovine intervertebral discs (bovine intervertebral discs (bIVD)).

For the characterization, Young's modulus or modulus of elasticity (Akhtar et. Al 2011) was determined locally on an established device (Biomomentum Mach-1 Biomomentum Inc.; Sim et al. 2014).

Figure 11:
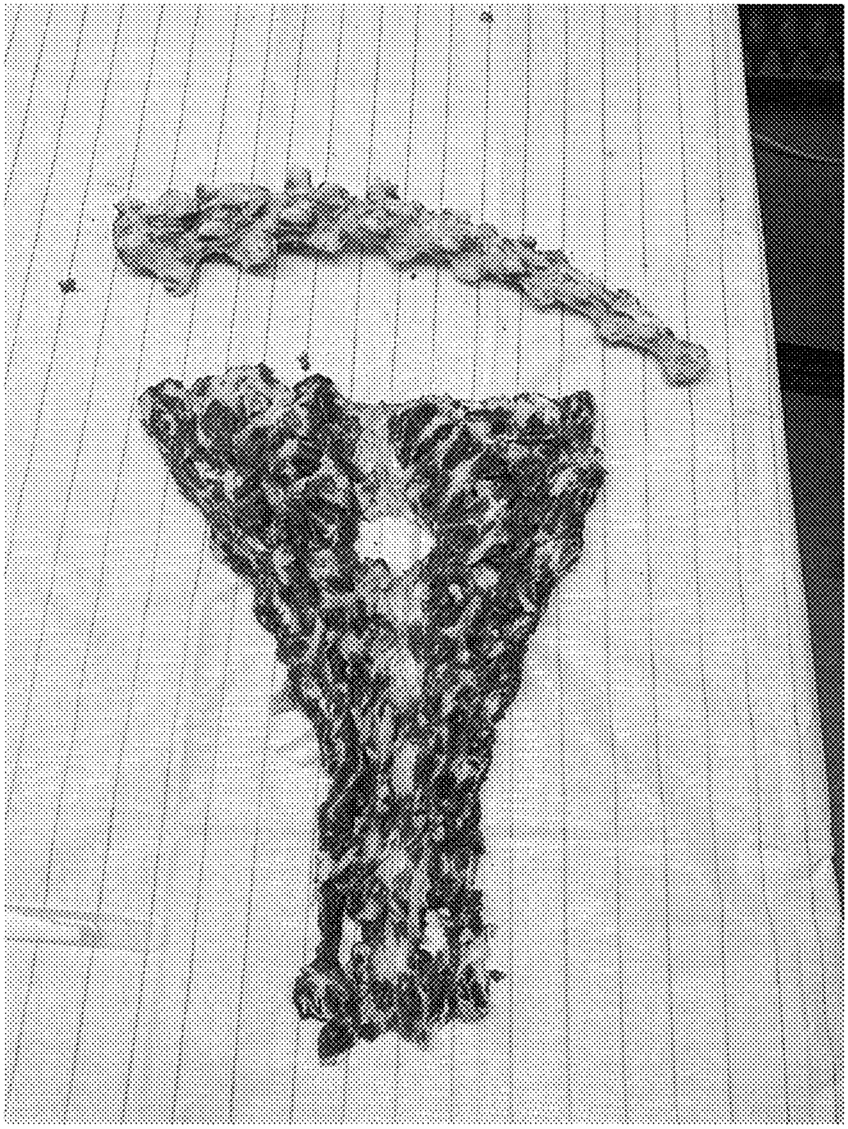

Fresh bovine tails were provided from the local meat processing plant within 2 hours of slaughter. The paravertebral structure was removed (FIG. 11).

Figure 12:

Bovine intervertebral discs (IVDs), which are attached to the vertebral body, were isolated (FIG. 12).

Figure 13:
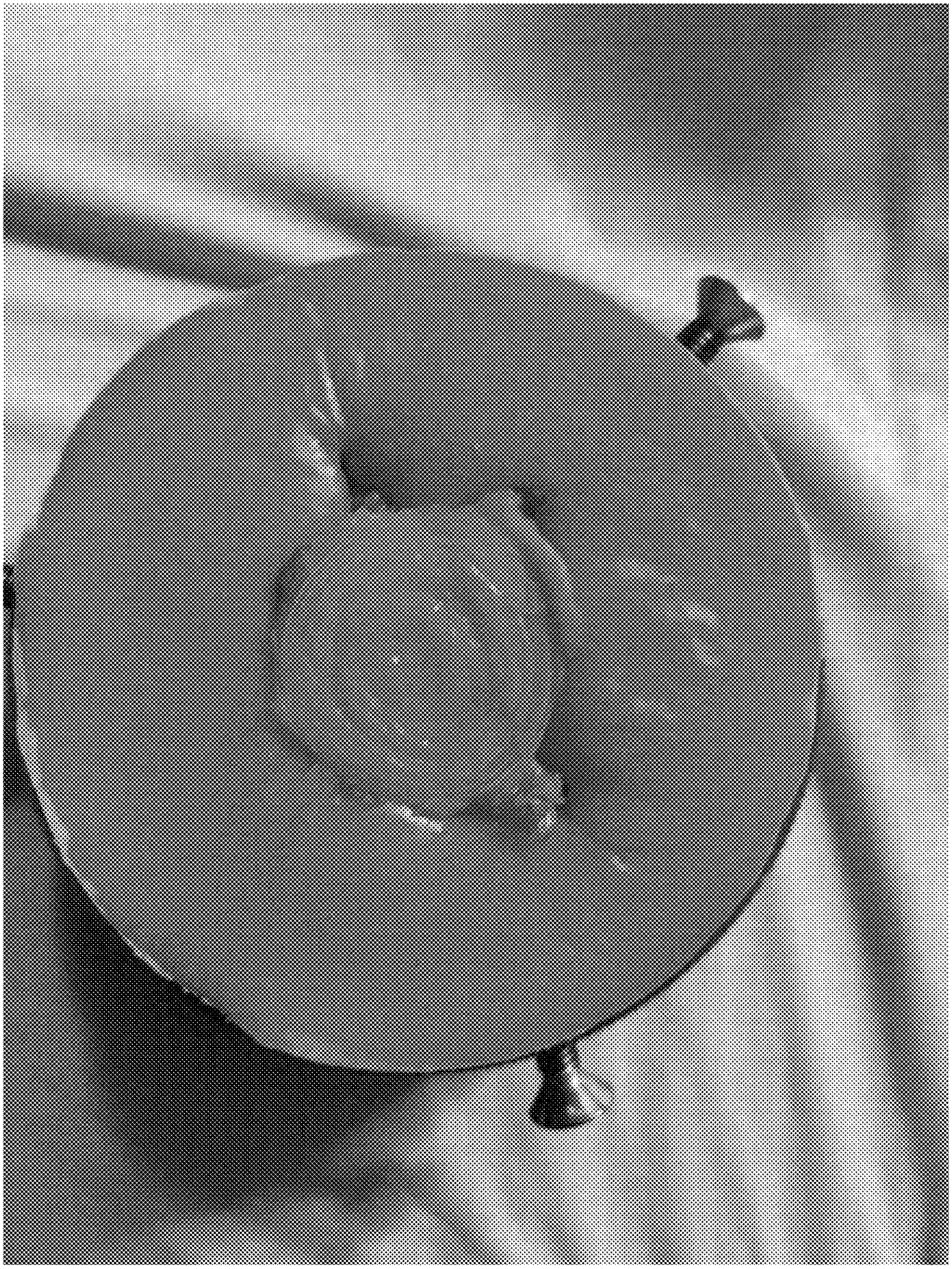

In order to stabilize the samples on the device, the bovine vertebral bodies with attached intervertebral discs were fixed in PMMA bone cement (FIG. 13).

Figure 14:
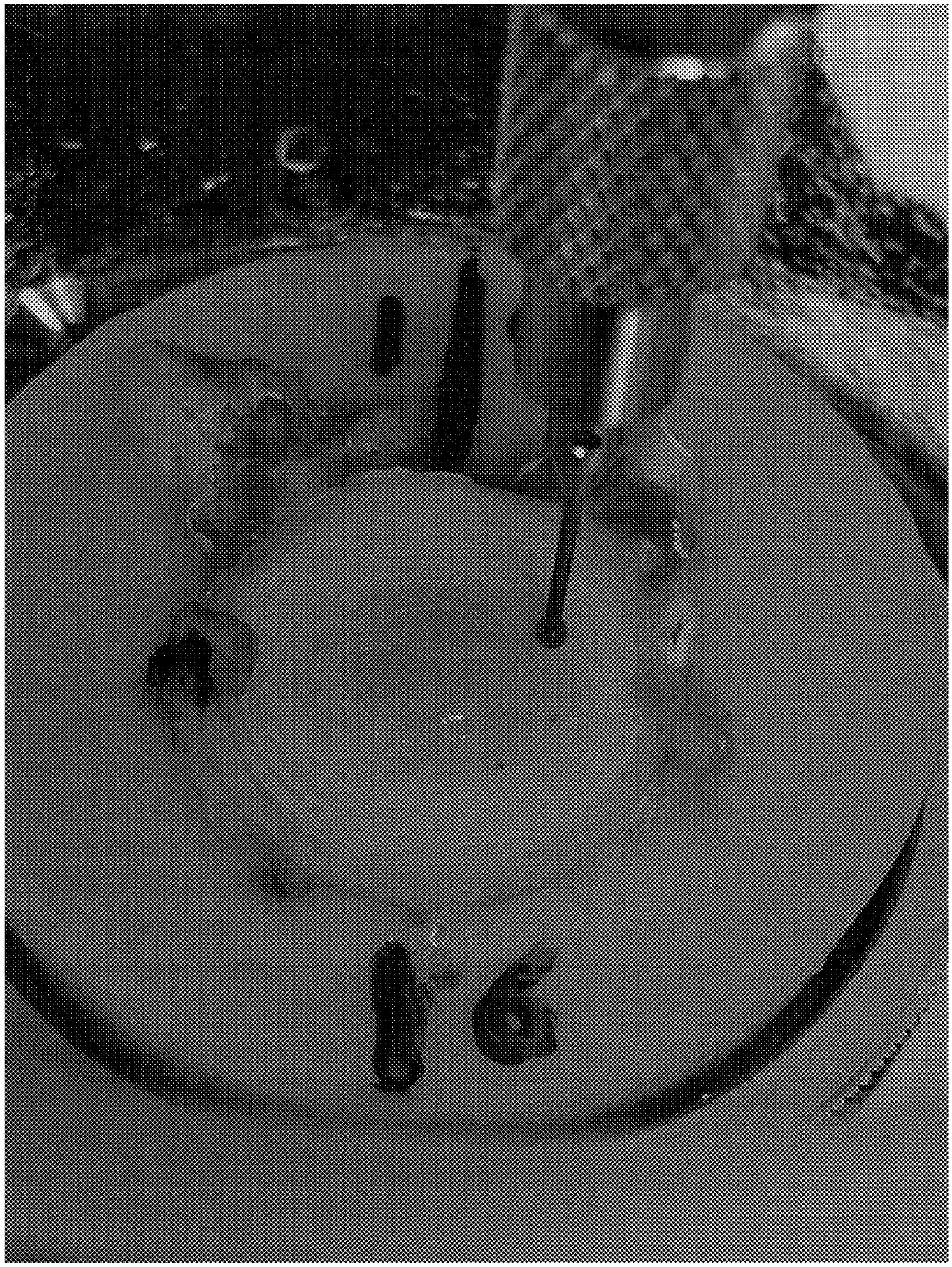
FIG. 14 Detection of the surface of the beef slices by means of the Biomomentum Mach-1

With the aid of the camera of the Biomomentum device, the surface of the bovine intervertebral discs was measured with respect to their biomechanical properties (Young's modulus) (FIG. 14).

In order to achieve comparable results, the samples were treated in a dark environment, such that activation of riboflavin by natural light sources can be excluded. A solution with 8 mM riboflavin (riboflavin 5'-phosphate sodium salt hydrate, Sigmaaldrich) in PBS (phosphate buffered saline solution) and pH: 7.4 water (Thermofisher) was used to soak the exposed surface of the bovine intervertebral discs for 15 minutes (dark mode). Immediately afterwards, the samples were placed in the Biomomentum device for analysis (dark mode).

After the analysis, the same sample was irradiated homogeneously with 365 nm UVA light (Opsytech Dr. Groebel-UV LED series L) at 3.5 mW/cm$^2$ for 15 minutes. A second analysis of the previously measured positions followed.

A total of 38 measurements were carried out on 15 healthy bovine intervertebral discs. Stiffening or reinforcement of the elastic properties (Young's modulus) was observed in all samples.

Figure 15:
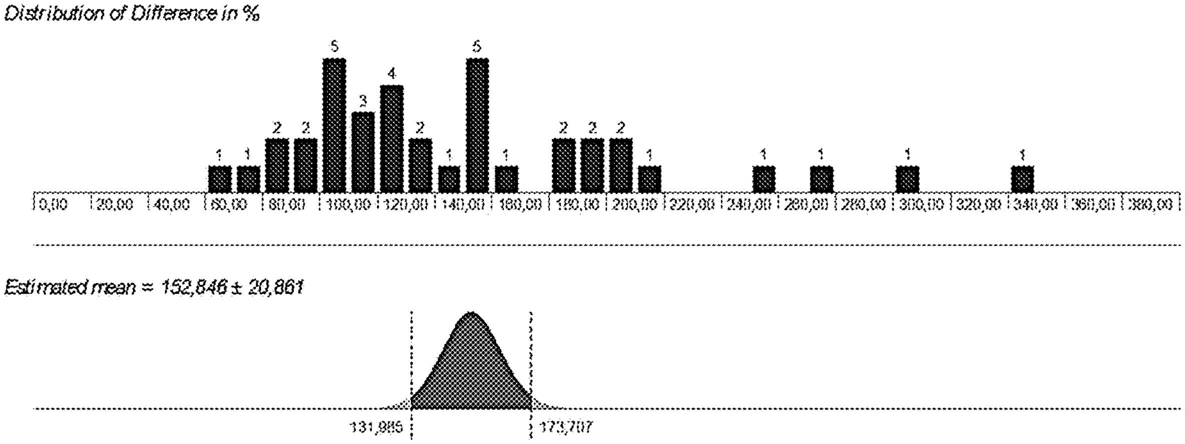
FIG. 15 Results for the percentage stiffening of the bovine intervertebral discs treated with UV irradiation in comparison to the controls.

The results for the individual samples are summarized as percentage stiffening in FIG. 15.

The percentage stiffening corresponds to the percentage increase in Young's modulus after UV irradiation, compared to the value measured before UV irradiation.

The minimum stiffening or reinforcement is 52%, while the maximum stiffening is 348%. The variability can in part be attributed to inhomogeneous absorption of riboflavin in the tissue due to the anisotropic distribution of proteoglycan in the bovine intervertebral discs.

In any case, this data also shows that by increasing the crosslinking density in the tissues, in-situ application of the riboflavin with subsequent irradiation can lead to improved overall stabilization of the intervertebral discs.

It is pointed out that various alternatives to the described embodiments of the invention can be used in order to carry out the invention and to arrive at the solution according to the invention. The riboflavin according to the invention or the pharmaceutical composition according to the invention for the treatment of a disease of amphiarthrotic, synarthrotic or diarthrotic joints, preferably an intervertebral disc disease, as well as the method and the kit are therefore not limited in their designs to the above preferred embodiments. Instead, a large number of design variants are conceivable, which can differ from the solution shown. The purpose of the claims is to define the scope of the invention.

The scope of protection of the claims is directed at using the riboflavin according to the invention or the pharmaceutical composition according to the invention for the treatment of a disease of amphiarthrotic, synarthrotic or diarthrotic joints, preferably an intervertebral disc disease, as well as the method and the kit are therefore not limited in their designs to the above preferred embodiments.

REFERENCES

Akhtar R., Michael J. Sherratt, J. Kennedy Cruickshank and Brian Derby, Characterizing the elastic properties of tissues, *Mater Today* (Kidlington). 2011 March; 14 (3): 96-105. doi: 10.1016/S1369-7021 (11) 70059-1

Choe E, Huang R, Min D B. Chemical Reactions and Stability of Riboflavin in Foods. *Journal of Food Science.* 2005; 70(1):R28-R36. doi:10.1111/j.1365-2621.2005.tb09055.x.

Dubietis, Audrius & Butkus, Rytis & Piskarskas, Algis. (2006). Trends in chirped pulse optical parametric amplification. Selected Topics in Quantum Electronics, IEEE Journal of. 12. 163-172.10.1109/JSTQE.2006.871962.

Finch P. Technology Insight: Imaging of low back pain. *Nature Reviews Rheumatology.* 2006; 2(10):554-561. doi: 10.1038/ncprheum0293.

Hafezi F, Mrochen M, Iseli H P, Seiler T. Collagen crosslinking with ultraviolet-A and hypoosmolar riboflavin solution in thin corneas. *Journal of Cataract & Refractive Surgery.* 2009; 35(4):621-624. doi:10.1016/j.jcrs.2008.10.060.

Huang R, Choe E, Min D B. Kinetics for Singlet Oxygen Formation by Riboflavin Photosensitization and the Reaction between Riboflavin and Singlet Oxygen. *Journal of Food Science.* 2004; 69(9):C726-C732. doi:10.1111/j.1365-2621.2004.tb09924.x.

Kuslich S D, Ulstrom C L, Michael C J, The tissue origin of low back pain and sciatica: a report of pain response to tissue stimulation during operations on the lumbar spine using local anestheisa. *Orthop. Clin. North Am.* 1991; 22: 181 1991.

LaBella F, Waykole P, Queen G. Formation of insoluble gels and dityrosine by the action of peroxidase on soluble collagens. *Biochemical and Biophysical Research Communications.* 1968; 30(4): 333-338. doi: 10.1016/0006-291X (68) 90746-8.

Mahgol Farjadnia M N. Corneal cross-linking treatment of keratoconus. *Oman Journal of Ophthalmology.* 2015; 8(2):86-91. doi:10.4103/0974-620X.159105.

McCall A S, Kraft S, Edelhauser H F, et al. Mechanisms of Corneal Tissue Cross-linking in Response to Treatment with Topical Riboflavin and Long-Wavelength Ultraviolet Radiation (UVA). *Invest Ophthalmol Vis Sci.* 2010; 51(1): 129-138. doi:10.1167/iovs.09-3738.

Min D B, Boff J M. Chemistry and Reaction of Singlet Oxygen in Foods. *Comprehensive Reviews in Food Science and Food Safety.* 2002; 1(2):58-72. doi:10.1111/j.1541-4337.2002.tb00007.x.

Sim S, Chevrier A, Garon M, Quenneville E, Yaroshinsky A, Hoemann C D and Buschmann M D Non-destructive electromechanical assessment (Arthro-BST) of human articular cartilage correlates with histological scores and biomechanical properties Osteoarthritis Cartilage, 22(11) 1926-35. (2014)

Waykole P, Heidemann E. Dityrosine in collages. *Connective Tissue Research.* 2009; 4(4):219-222. doi:10.3109/03008207609152224.

Wollensak G, Spoerl E, Seiler T. Stress-strain measurements of human and porcine corneas after riboflavin-ultraviolet-A-induced cross-linking. *Journal of Cataract & Refractive Surgery.* 2003; 29(9):1780-1785. doi:10.1016/S0886-3350(03)00407-3.

Wollensak G. Crosslinking treatment of progressive keratoconus: new hope. *Current Opinion in Ophthalmology.* 2006; 17(4):356-360-360. doi:10.1097/01.icu.0000233954.86723.25.

What is claimed is:

1. A method of treatment of a patient with a disease of a diarthrotic, amphiarthrotic or synarthrotic joint comprising:

providing riboflavin and a pharmaceutical carrier, wherein the pharmaceutical carrier relates to a material in liquid form as a solution, which does not interfere with the action of riboflavin;

locally administering riboflavin into a collagenous tissue of the joint, wherein the local administration comprises an injection of the riboflavin and the pharmaceutical carrier into the collagenous tissue of the joint; and irradiating the collagenous tissue with electromagnetic radiation and stiffening the collagenous tissue of the joint by at least 52%.

2. The method of treatment according to claim 1, characterized in that the radiation is UV radiation.

3. The method of treatment according to claim 1, characterized in that the irradiation takes place at a wavelength of more than 700 nm, wherein pulsed radiation takes place, such that a crosslinking reaction mediated by riboflavin is brought about by non-linear optical effects.

4. The method of treatment according to claim 1, characterized in that the disease is an intervertebral disc disease and the local administration of riboflavin and subsequent irradiation takes place at the site of the disease on the intervertebral disc.

5. The method of treatment according to claim 1, characterized in that the UV irradiation takes place at a wavelength between 200 and 400 nm, and/or a radiation intensity of 0.1 mW to 500 mW.

6. The method of treatment according to claim 1, characterized in that the irradiation takes place with pulses of a wavelength of more than 700 nm with a pulse duration in the range of nanoseconds or femtoseconds.

7. The method of treatment according to claim 1, characterized in that the pulse duration is in the range from 10 fs to 500 fs, and/or the irradiation takes place at a wavelength in the range from 700 nm to 820 nm.

8. The method of treatment according to claim 6, characterized in that the repetition rate of the pulses is 1 kHz to 1000 kHz, and/or the energy per pulse is 100 nJ to 50 μJ (joule).

9. The method of treatment according to claim 6, characterized in that the irradiation takes place with a radiation intensity in the range from 0.1 mW to 1000.

10. The method of treatment according to claim 1, characterized in that the irradiation is started after a period of 10 sec to 30 min, following the local administration of the riboflavin and takes place for a period of 10 sec to 30 min.

11. The method of treatment according to claim 1, wherein the riboflavin is provided in a pharmaceutical composition for use as a medicament in the treatment of a disease of a diarthrotic, amphiarthrotic or synarthrotic joint, comprising:

a) the riboflavin, and b) a pharmaceutical carrier and wherein the pharmaceutical composition is locally administered into a collagenous tissue of the joint by injection; and wherein the pharmaceutical carrier relates to a material in liquid form as a solution, which does not interfere with the action of riboflavin.

12. The method of treatment according to claim 11, characterized in that the pharmaceutical carrier is a hypoosmolar solution.

13. The method of treatment according to claim 11, characterized in that riboflavin is present in the pharmaceutical composition at a concentration of 0.01% by weight to 5% by weight.

14. A kit for treating a patient with a disease of a diarthrotic, amphiarthrotic or synarthrotic joint, comprising:

a pharmaceutical composition comprising riboflavin and a pharmaceutical carrier, wherein the pharmaceutical carrier relates to a material in liquid form as a solution, which does not interfere with the action of riboflavin;

an injection device suitable for injection into a collagenous tissue of the joint;

a radiation device; and instructions for the treatment of a patient in situ by local administration of riboflavin in a collagenous tissue of the joint by injection and subsequent exposure to radiation wherein the collagenous tissue of the joint is stiffened by at least 52%.

15. The method of treatment according to claim 1 characterized in that the disease is an intervertebral disc disease, and the treatment comprises local administration of riboflavin by injection of the riboflavin and the pharmaceutical carrier into the annulus fibrosus and/or the nucleus pulposus.

16. The method of treatment according to claim 1 characterized in that the stiffening corresponds to the percentage increase in a modulus of elasticity of the tissue after compared to prior irradiating the collagenous tissue.

* * * * *